United States Patent [19]

Crane

[11] Patent Number: 4,936,295
[45] Date of Patent: * Jun. 26, 1990

[54] LATERAL SUPPORT FOR ANKLE

[76] Inventor: Larry A. Crane, 263 River Road, Franklin, N.C. 28734

[*] Notice: The portion of the term of this patent subsequent to Mar. 7, 2006 has been disclaimed.

[21] Appl. No.: 303,563

[22] Filed: Jan. 27, 1989

Related U.S. Application Data

[63] Continuation-in-part of Ser. No. 99,559, Sep. 22, 1987, Pat. No. 4,809,686.

[51] Int. Cl.$^5$ .............................................. A61F 5/00
[52] U.S. Cl. .................................... 128/80 H; 36/89; 128/166
[58] Field of Search ................. 128/80 H, 80 R, 80 F, 128/166; 36/88, 89, 90

[56] References Cited

U.S. PATENT DOCUMENTS

| | | | |
|---|---|---|---|
| 246,984 | 9/1881 | Stillman | 128/80 H |
| 2,477,591 | 8/1949 | Follis | 128/80 H |
| 2,525,658 | 10/1950 | Dumelin | 128/80 H |
| 4,809,686 | 3/1989 | Crane | 128/80 H |

FOREIGN PATENT DOCUMENTS

| | | | |
|---|---|---|---|
| 293765 | 8/1916 | Fed. Rep. of Germany | 128/80 H |
| 381291 | 9/1923 | Fed. Rep. of Germany | 128/80 H |

Primary Examiner—Edgar S. Burr
Assistant Examiner—Moshe I. Cohen
Attorney, Agent, or Firm—Shefte, Pinckney & Sawyer

[57] ABSTRACT

An ankle support prevents damage to a person's ankle by preventing severe lateral bending of the ankle. A support bar is pivotally attached to a high-top shoe, with the upper end of the bar well above the ankle and the lower end of the bar just below the foot. The upper end of the bar is fixed about centrally of the leg, while the lower end of the bar is fixed just forward of the heel. This results in having the bar pass along the front portion of the ankle. Both ends of the support bar can move somewhat at their connection points, so normal foot movement is not restricted while severe lateral motion is prevented. One aspect of the ankle support includes means for automatically adjusting the effective length of the ankle support between the attachment location above the ankle and the attachment location below the ankle.

16 Claims, 7 Drawing Sheets

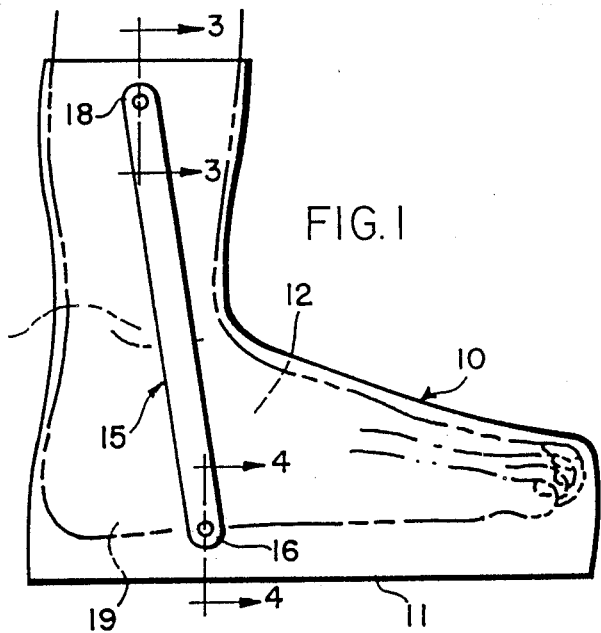
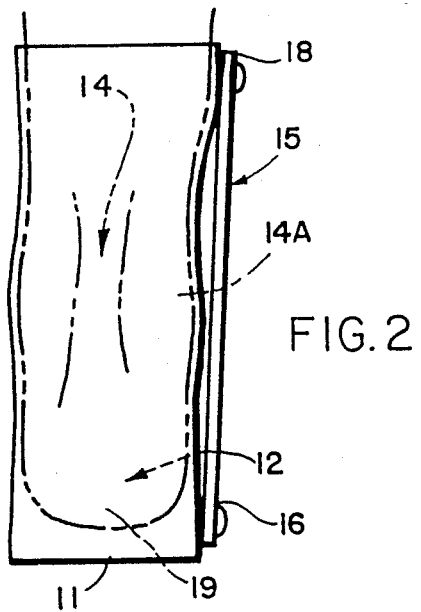

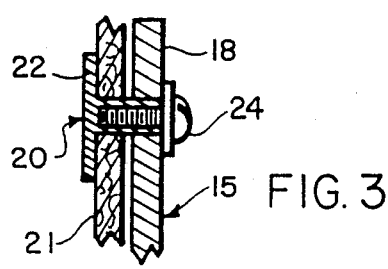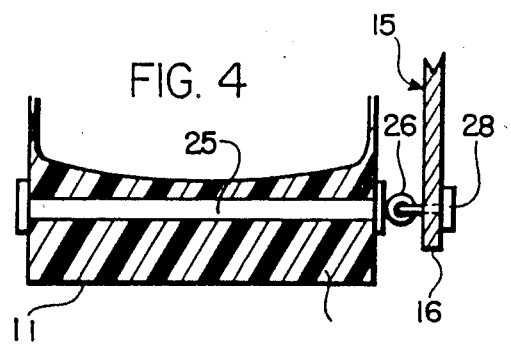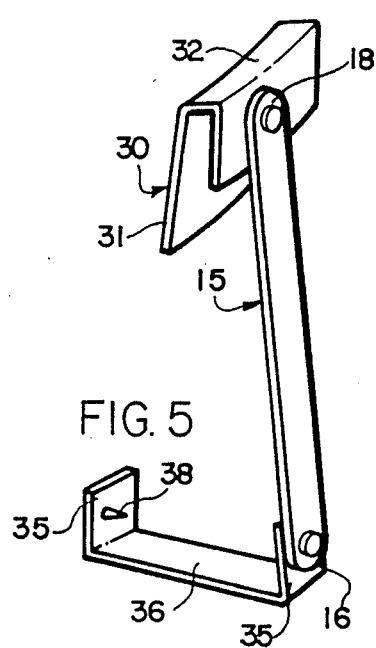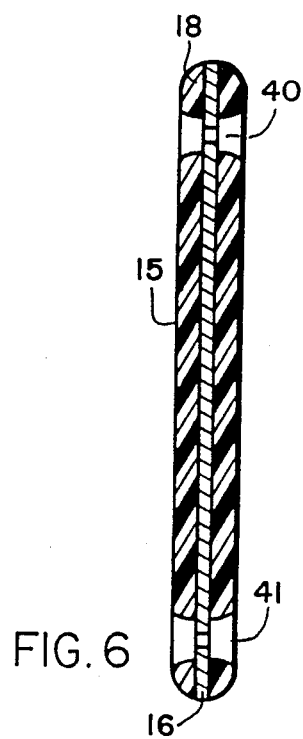

LATERAL SUPPORT FOR ANKLE

CROSS-REFERENCE TO RELATED APPLICATION

This is a continuation-in-part of application Ser. No. 099,559, filed Sept. 22, 1987 now U.S. Pat. No. 4,809,686

BACKGROUND OF THE INVENTION

The numerous undertakings, a person's ankle is subject to lateral forces to a hazardous degree. The most common attempt to prevent damage by these lateral forces include the use of heavy shoes or boots to support the ankles, and the wrapping of the ankle with gauze or tape. All these efforts at supporting the ankle are insufficient when the ankle is subject to strong lateral forces, or strong forces tending to fold the ankle in the lateral direction.

Another prior art effort at supporting the ankle against lateral motion is through the use of a generally rigid member attached above and below the ankle and spanning the ankle. These devices also have not been successful, the more common reasons for failure including improper length and placement of the rigid member. Additionally, the prior art ankle supports have not been appropriately attached to yield the needed support.

For example, in U.S. Pat. No. 4,103,897 to Ostyn, a stance correction device is disclosed having a rigid strip member having an upper end portion received in a pocket above the ankle and a bottom end portion pivotably connected to an L-shaped member, the strip member pivoting in a rocking movement parallel to the shoe to which the L-shaped member is fastened. The Ostyn device is adapted for the limited function of restraining the leg above the ankle from outward movement—this is, movement away from the leg—when a golfer starts his golf swing and causes his ankle to bend outwardly. However, the Ostyn design is not particularly suitable for providing ankle support through a wide range of extreme movements, which could cause injury to the ankle, while still permitting essentially unencumbered natural movement of the foot and ankle during even the most strenuous and active types of physical activities, such as basketball, leading to the extreme movements.

In view of the unsuccessful prior art efforts, there is still a need to provide an ankle support to protect the ankle against strong forces tending to bend the ankle laterally without unduly restricting motion of the foot.

SUMMARY OF THE INVENTION

This invention relates generally to ankle supports, and is more particularly concerned with a floating support member for preventing damage to the ankle from excessive bending in a lateral direction.

The present invention provides a rigid member anchored at a point above the ankle and at a point below the ankle and forwardly thereof. The rigid member extends above the ankle and below the ankle, spanning the ankle to provide mechanical support. Each end of the support member is fixed, preferably to a shoe or the like, in a resilient or floating manner.

The support of the present invention extends generally across the forward portion of the ankle, and is so located that, when the foot is moved upwardly, the support member remains sufficiently in the vicinity of the ankle to provide needed support, and when the foot is moved downwardly the support also remains sufficiently in the vicinity of the ankle to provide the needed support against lateral forces.

The present invention provides, in one aspect, a coupling means associated with the rigid support member, the retaining means for attaching the ends of the rigid support member above and below the ankle, or both the support member and the retaining means, for automatically changing the effective length of the support member between the two attachment locations during normal movements of the ankle. The coupling means permits variations in the distance between the attachment location above the ankle and the attachment location below the ankle so that the support member can continuously extend in an essentially straight line along a predetermined portion of the ankle to prevent lateral bending thereof while permitting a wide range of variations in the spacing between the two attachment locations due to normal movement of the leg relative to the foot. By providing a rigid member that is fixed in place both above and below the ankle to positively prevent any lateral bending of the ankle, the support of the present invention provides an ankle support which operates reliably through virtually unrestricted normal movement of the foot during even strenuous activities. Thus, the support of the present invention overcomes the limitations of the prior art by providing an ankle support which remains appropriately positioned to prevent any lateral bending of the ankle through virtually unrestricted normal movement of the foot.

BRIEF DESCRIPTION OF THE DRAWINGS

These and other features and advantages of the present invention will become apparent from consideration of the following specification when taken in conjunction with the accompanying drawings in which:

FIG. 1 is a side elevational view showing a shoe with an ankle support made in accordance with the present invention carried on the shoe, and a foot shown in phantom;

FIG. 2 is a rear elevational view of the shoe illustrated in FIG. 1;

FIG. 3 is an enlarged cross-sectional view taken substantially along the line 3—3 in FIG. 1;

FIG. 4 is an enlarged cross-sectional view taken substantially along the line 4—4 in FIG. 1;

FIG. 5 is a perspective view showing a support member made in accordance with the present invention, and including means for selectively attaching the support member to a shoe;

FIG. 6 is a longitudinal cross-sectional view through a support member showing optional padding for the support member.

DETAILED DESCRIPTION OF THE EMBODIMENTS

Figure 8:
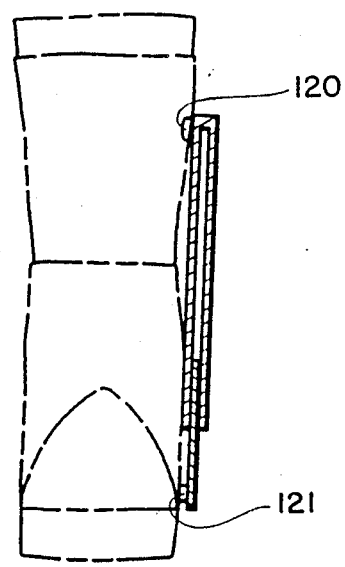
FIG. 8 is a rear elevational view of the shoe and the ankle support illustrated in FIG. 7.

Referring now more particularly to the drawings, and to those embodiments of the invention here presented by way of illustration, FIG. 1 is a somewhat schematic view, illustrating generally a high-top shoe designated at 10 having a sole 11. A foot is shown in broken lines since the ankle support of the present invention is to be placed appropriately relative to the foot for maximum protection. Thus, it will be seen that the foot is designated generally at 12, while the ankle is shown at 14.

It will be understood by those skilled in the art that the ankle is not a single point or a single bone. Thus, for the present discussion some definitions need to be provided. The ankle as a whole is a joint that allows the foot to move with respect to the leg. The protuberances that are popularly called the ankle are parts of the tibia and fibula, the tibia providing the inside protuberance and the fibula providing the outside protuberance. These protuberances will be referred to as the inside ankle (tibia) and the outside ankle (fibula), and the general term ankle will apply to the joint as a whole.

The support member is indicated at 15 and is shown as comprising a strip of material, such as steel or the like. While the specific material is not important, one must select a material having sufficient strength to withstand the forces to be encountered. The support member 15 is fixed to the shoe 10 approximately in the vicinity of the shoe sole 11, and below the foot 12. The upper end 18 of the support 15 is fixed to the side of the shoe 10 at a point definitely above the ankle 14. As will be seen in FIG. 1, the upper end 18 of the support 15 is substantially centrally of the profile of the leg, or shoe 10, while the lower end 16 of the support member 15 is somewhat forwardly of the leg. The lower end 16 of the support member 15 will generally be located just forward of the heel 19 of the foot 12, approximately on the line between the tarsals and the metatarsals.

It will be realized that, as the foot 12 is moved to pivot at the ankle 14, the lower end 16 of the support member 15 will move, rotating about the end 18. To some extent, the mechanical arrangement is such as to allow such motion without interference. Nevertheless, realizing that the motion of the foot will not constitute a precise pivotal motion at the ankle, and that the ankle does not constitute a truly precise mechanical pivot, it will be realized that the support member 15 must allow some movement of the shoe 10 with respect to the support member 15. Such motion is contemplated in the present invention.

Looking now at FIG. 2 of the drawings, the shoe 10 is again shown in full lines with the foot 12 shown in phantom. In FIG. 2 it will be seen that the lower end 16 of the support 15 is below the heel 19, and the upper end 18 of the support 15 is above the ankle 14. The length of the support member 15 must be sufficient to extend above and below the ankle to give an adequate mechanical advantage in supporting the ankle.

Continuing to look at FIG. 2 of the drawings, it should be understood that, if there is a force tending to cause the foot 12 to bend at the ankle 14, the ankle 14 will bear against the support member 15 trying either to bend the member 15 or to remove the end 16 and/or 18 from the connection to the shoe. With this in mind, it should be understood that, if the lower end 16 is firmly attached to the shoe and the outside ankle 14A is urged against the support member 15, and the end 16 acts as a fulcrum while the outside ankle 14A acts as the force, then the upper end 18 plays the part of the resistance. With this analysis, it will be understood that in the distance between the ankle 14 and the upper end 18 is very short, the force of the outside ankle 14A against the support member 15 will have a mechanical advantage in moving the upper end 18. The motion of the upper end 18 may be in the form of tearing the end from its connection, and may result simply in sufficient distortion of the shoe that the foot 12 can move within the shoe. Regardless of the particular form of the failure, the ankle 14 is subject to damage.

With the foregoing in mind, it will be clear that the upper end 18 of the support 15 may be as far up the leg as one desires, though the connection should be below the knee for obvious mechanical reasons. The preferred embodiment, however, will place the upper end 18 of the support 15 generally at the top of fairly conventional high top shoes or boots.

Looking now at FIG. 3 of the drawings, it will be seen that one form of connection of the support member 15 to the shoe is to provide a threaded fitting 20 extending through the material 21 of the shoe 10. Though not here shown, it is contemplated that reinforcement in the form of molded plastic member, stitching or the like will be used around the hole 22 through which the fitting 20 passes. A screw 24 then extends through the upper end 18 of the support member 15 to be received by the threaded fitting 20.

With this arrangement, it will be understood that the material 21 is flexible, and may be leather, canvas or the like. The fact that the material 21 is flexible will allow the fitting 20 to vary somewhat, hence allow the upper end 18 of the support 15 to move, or float.

Looking at FIG. 4 of the drawings, a slightly different arrangement is shown for connection of the support member 15 to the shoe 10. In FIG. 4 there is a pin 25 passing through the sole 11 of the shoe 10, the pin 25 terminating in a loop 26. The support member 15 is then provided with a mating loop member 28. With the two loops, or eyes, engaging each other it will be understood that there is sufficient play in the joint to allow the desired floating of the support member 15.

Those skilled in the art will devise numerous connections for fixing the support member 15 to shoes or the like, and the two above described connections are by way of illustration only.

Attention is now directed to FIG. 5 of the drawings which discloses a connection means that will allow a user to fix the support member to a selected pair of shoes. The support member is again designated at 15, with an upper end 18 and a lower end 16. The upper end 18 of support member 15 is pivotally connected to a clip designated at 30, the clip 30 being somewhat curved as viewed from the top, and having an inner flange 31 that is adapted to be received with a boot. The upper curved portion 32 than spans the upper edge of the boot while the outer flange 34 lies along the outside of the boot and provides for connection of the support member 15.

The lower end 16 of the support member 15 is pivoted to an upwardly turned flange 35, the flange 35 being one of a pair of such flanges connected by a transverse member 36. It will be seen that the flanges 35 include inwardly projecting members such as the member 38 to engage a shoe.

From the above discussion, it should be understood that the transverse member 36 will be placed beneath the shoe, adjacent to the heel of the shoe. The flanges 35 will then extend upwardly at each side of the shoe and the inward projections 38 will engage the sole of the shoe sufficiently to prevent dislocation of the members. The clip 30 will engage the upper portion of the shoe or boot, and it will be seen that the inner flange 31 is long enough that the clip will not be easily removed from the boot.

With this in mind, it will be seen that lateral forces against the support member 15 will be restrained by the inner flange 31 of the clip 30, and by the flanges 35 of the lower member.

When the support member of the present invention is utilized in some environments, the support member may take the form of a simple metal member as is shown in FIGS. 1–5 of the drawings. In some situations, such as in sporting events and the like, it may be desirable to provide some form of padding for the support member, either on the outside to protect other participants, or on the inside to protect the wearer. Such an arrangement is shown in FIG. 6 of the drawings where it will be seen that expanded plastic material is shown covering both sides of the support member 15. Appropriate openings 40 and 41 are provided in the vicinity of the holes in the upper end 18 and lower end 16. Those skilled in the art will therefore understand that foamed plastic such as polyurethane or the polyolefins may be utilized, sheets of material or fibrous padding may be utilized, and of course, rubber, either foamed or not may be used. Further, various forms of covering may be provided for the support member 15, both for utilitarian and for aesthetic purposes.

While some of the prior art ankle supports have rendered the supports very wide in the vicinity of the ankle, it should be noted that the additional width appears to serve no utilitarian function. It is the strength substantially along the line between the upper and lower connections that is important, and this fact renders it important to place the support member 15 substantially as shown in FIG. 1 of the drawings. As was discussed briefly, the support member 15 should be placed somewhat at the forward portion of the ankle 14 so that, as the foot is moved up the support member 15 will remain in the vicinity of the ankle 14, and as the foot is moved down the support member 15 will still remain in the vicinity of the ankle 14 to provide the needed support.

In FIG. 1, the support 15 is places on the outside of the shoe 10 so the support 15 extends along the forward position of the outside ankle 14A. If the support 15 is placed on the inside of the shoe, the support will be located to extend along the forward portion of the inside ankle 14B. It is also contemplated that supports 15 may be placed both inside and outside, though it appears that the use of only one support 15 is highly satisfactory.

It will of course be understood that the support member 15 may be made wider, or in the form of struts or the like, or in various other forms for aesthetic purposes. Further, trademarks and the like may be painted on the support, or worked into the struts making up the support as desired.

Figure 7:
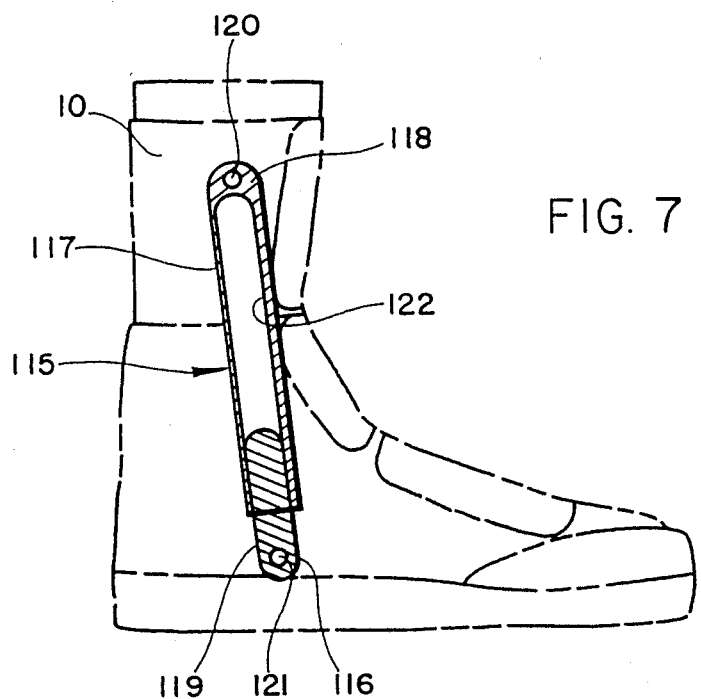
FIG. 7 is a side elevational view showing a shoe with another embodiment to the ankle support of the present invention mounted to the shoe.

In FIGS. 7 and 8, another embodiment of the invention is illustrated and includes a support member 115 secured to the shoe 10 for supporting the ankle 14 within the shoe 10 and having a first portion 117 defining the upper end 118 of the support member and a second portion 119 defining the lower end 116 of the support member. The upper end 118 is attached above the ankle at a first attachment location and the lower end 116 is attached below the ankle at a second attachment location by a retaining means which includes a pivotal connector 120 associated with the upper end 118 and a pivotal connector 121 associated with the lower end 116. Specifically, the upper end 118 is pivotally connected to the shoe 10 by the pivotal connector 120 and the lower end 116 is pivotally connected to the shoe 10 by the pivotal connector 121. The first portion 117 and the second portion 119 of the support member 115 are movably coupled to one another by a coupling means which includes an open end slot 122 in the first portion 117 opening at the free end of the first portion 117 and extending longitudinally of the first portion 117. The slot 122 and the second portion 119 are compatibly configured so that the second portion 119 is slidably carried within the slot 122. As can be understood, the first portion 117 slides relative to the second portion 119 when either the first portion 117 and the second portion 119 are pivoted about their respective pivotal connections with the shoe 10.

Due to the sliding movement of the first portion 117 of the support member 115 relative to the second portion 119 of the support member, the effective length of the support member between the pivotal connectors 120 and 121 is automatically changed during normal movements of the ankle to thereby permit variations in the distance between the two pivotal connectors and permitting the support member to extend in an essentially straight line along a predetermined portion of the ankle to prevent lateral bending thereof during normal movements of the ankle notwithstanding variation in spacing between the two pivotal connectors that may be caused by the ankle movement. Specifically, movement of the ankle in a forward direction causes the second portion 119 to slide toward the base of the slot 222, thereby automatically reducing the effective length of the support member 115 between the pivotal connectors 120 and 121. Alternatively, movement of the ankle in a backward direction causes the second portion 119 to slide in the direction away from the base of the slot 122 so that the effective length of the support member 115 is automatically increased between the pivotal connectors 120,121.

Figure 10:
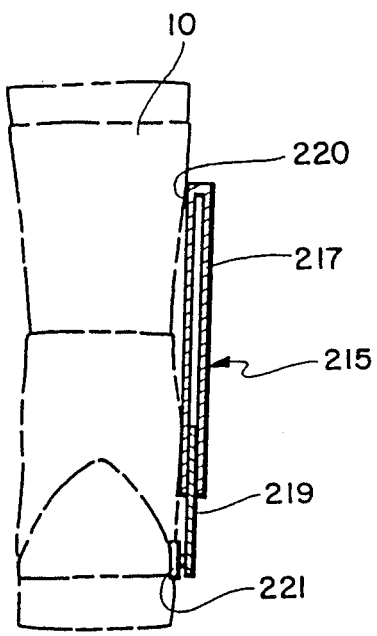
FIG. 10 is a rear elevational view of the shoe and the ankle support illustrated in FIG. 9.
Figure 9:
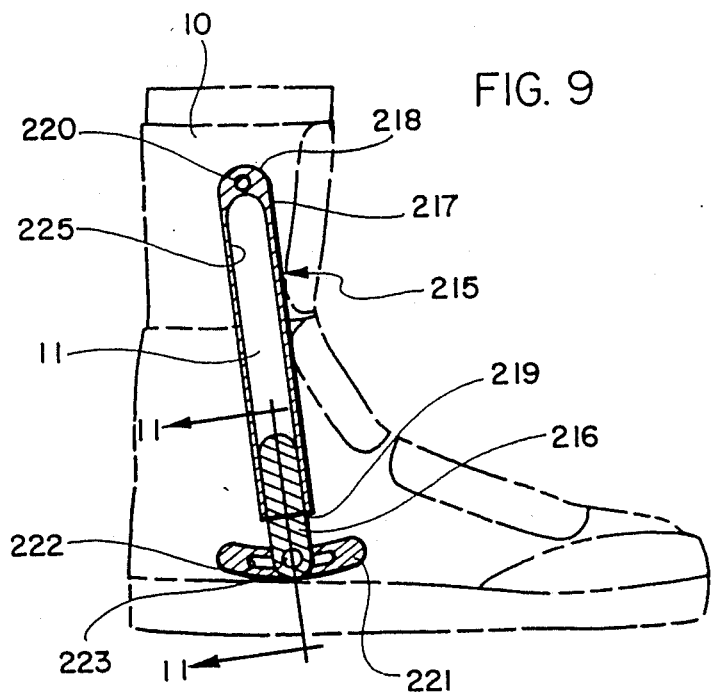
FIG. 9 is a side elevational view showing a shoe with a further embodiment of the ankle support of the present invention mounted to the shoe.
Figure 11:
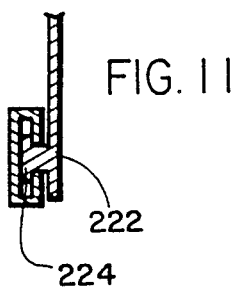
FIG. 11 is an enlarged cross-sectional view taken along line 11—11 in FIG. 9.

In FIGS. 9–11, a further embodiment of the invention is illustrated and includes a support member 215 secured to the shoe 10 for supporting the ankle 14 within the shoe 10 and having a first portion 217 defining the upper end 218 of the support member and a second portion 219 defining the lower end 216 of the support member. The first portion 217 is pivotally connected to the shoe 10 by a pivotal connector 220. The second portion 219 is connected to the shoe 10 by a slot member 221 having an arcuate slot 222 formed therein, and a attachment pin 223 fixedly coupled to the second portion 219. As seen in FIG. 11, the attachment pin 223 includes an enlarged head 224 at one end thereof and the attachment pin and its enlarged head are configured with respect to the arcuate slot 222 such that the cross-sectional area of the enlarged head 224 is slightly larger than the widthwise extent of the slot 222 as measured perpendicular to the arcuate extent of the slot. Additionally, the portion of the attachment pin 223 extending from the enlarged head 224 has a cross-sectional area less than the widthwise extent of the slot 222. As can be understood, the attachment pin 223 is movably retained within the slot 222 with the enlarged head 224 and the second portion 219 disposed on opposite sides of the slot 222.

The support member 215 additionally includes means for movably coupling the first portion 217 to the second portion 219, the coupling means including an open end slot 225 extending longitudinally of the first portion 217 from the free end thereof. The slot 225 is compatibly configured with the second portion 219 such that the second portion 219 is slidably received within the slot. As can be appreciated, as the foot 12 pivots at the ankle 14, the boot shoe 10 moves or flexes in correspondence therewith. In response to flexing of the shoe 10, several components of the support member 215 may move relative to one another and relative to the shoe 10. The first portion 217 may pivot about the pivotal connection 220. The second portion 219 may slide relative to the slot member 221 as the attachment pin 223 slides within the slot 222. Additionally, the second portion 219 may slide within the slot 225 of the first portion 217. Through a combination of all or some of the above-described relative movements, the axial length and the position of the support member 215 relative to the shoe 10 is responsively adjusted so that the support member 215 continuously extends in an essentially straight line along the forward portion of the ankle 14 and permits generally unrestricted normal axial movements of the foot 12 while resisting lateral bending of the ankle. For example, if the ankle is moved in the forward direction, the first portion 217 may pivot about the pivotal connection 220 while the second portion 219 may slide toward the base of the slot 225. Additionally, the forward movement of the ankle may cause the slot attachment pin 223 to slide in a rearward direction along the slot 222. These relative movements automatically reduce the effective length of the support member 215 to permit variations in the distance between the pivotal connection 220 and the attachment pin 223, whereby the support member extends in an essentially straight line along a predetermined portion of the ankle to prevent lateral bending thereof notwithstanding variations in the spacing between the pivotal connection 220 and the attachment pin 223.

Figure 13:
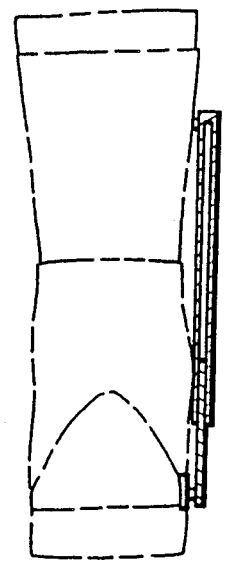
FIG. 13 is a rear elevational view of the shoe and the ankle support illustrated in FIG. 12.
Figure 12:
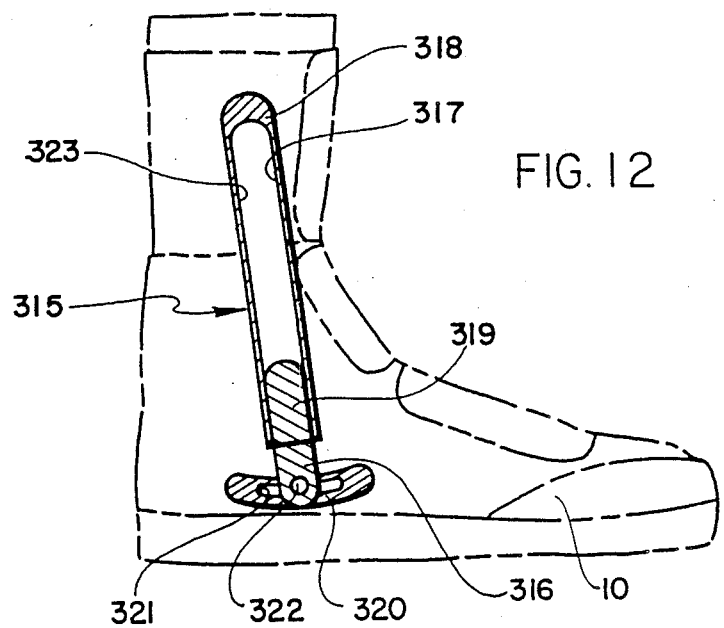
FIG. 12 is a side elevational view showing a shoe with yet another embodiment of the ankle support of the present invention mounted to the shoe.

In FIGS. 12 and 13, another embodiment of the invention is illustrated and includes a support member 315 secured to the shoe 10 for supporting the ankle 14 within the shoe 10 and having a first portion 317 defining the upper end 318 thereof and a lower portion 319 defining the lower end 316 thereof. The second portion 319 is movably coupled to the shoe 10 by a slot means including a slot member 320 fixedly attached to the shoe 10 and having an arcuate slot 321 therein and a attachment pin 322 fixedly attached to the second portion 319. The attachment pin 322 includes an enlarged head (not shown) which cooperates with the slot 321 to movably retain the attachment pin 322 in the slot 321, in a manner similar to the retention of the attachment pin 223 within the slot 222 as described above.

The first portion 317 is fixedly attached to the shoe 10 by adhesive or other appropriate attachment means. Additionally, the first portion 317 includes an open end slot 323 extending longitudinally thereof from the free end thereof. The slot 323 is compatibly configured with the second portion 319 such that the second portion 319 is slidably carried in the slot 323. Accordingly, when the ankle moves, for example, in a forward direction, the second portion 319 slides towards the base of the slot 323, thereby automatically reducing the effective length of the support member 315 to permit variations in the distance between the fixed attachment of the first portion 317 to the shoe 10 and the attachment pin 322. The attachment pin 322 slides as necessary within the slot 321 to accommodate changes in the inclination of the second portion 319 with respect to the slot.

Figure 18:
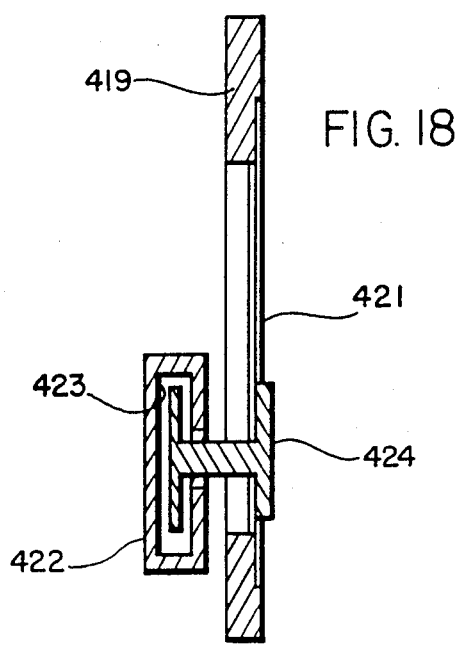
FIG. 18 is a vertical sectional view taken along lines XVIII—XVIII of FIG. 14 and showing the slot and attachment pin arrangement of the ankle support.
Figure 15:
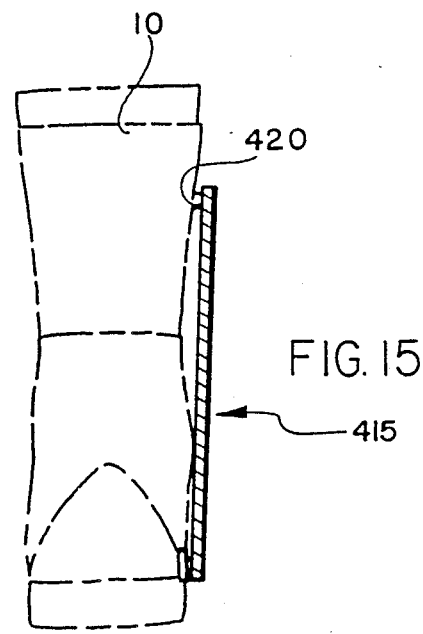
FIG. 15 is a rear elevational view of the shoe and the ankle support illustrated in FIG. 14.
Figure 14:
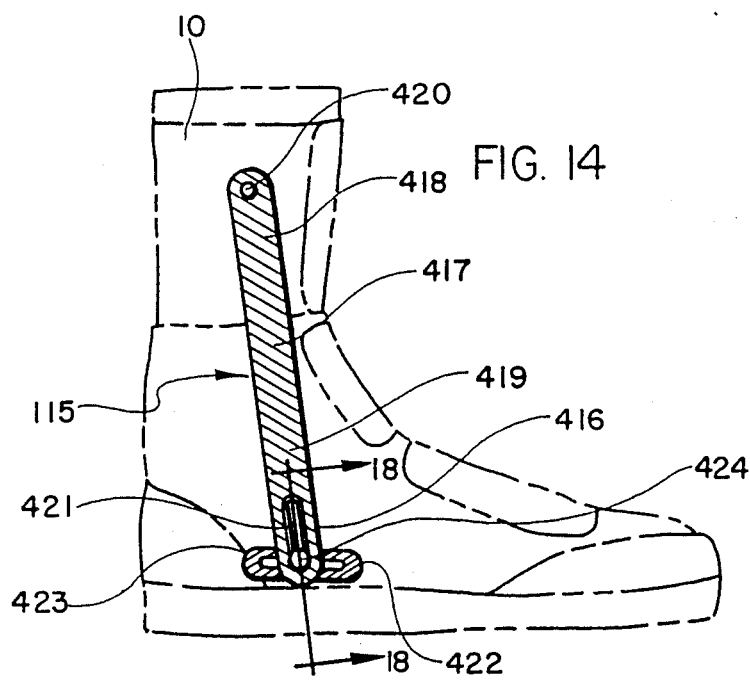
FIG. 14 is a side elevational view showing a shoe with a further embodiment of the ankle support of the present invention mounted on the shoe.

In FIGS. 14, 15 and 18, a further embodiment of the invention is illustrated and includes a support member 415 secured to the shoe 10 for supporting the ankle 14 within the shoe 10 and having a first portion 417 defining the upper end 418 thereof and a lower portion 419 defining the lower end 416 thereof. The first portion 417 is pivotally connected to the shoe 10 by a pivotal connector 420. The support member 415 is preferably formed as a single piece and includes a slot 421 formed therein and extending longitudinally within its lower portion 419. A slot member 422 defining a slot 423 is fixedly attached by adhesive or other appropriate securing means to the shoe 10. An attachment pin 424 having an enlarged head at each end thereof (see FIG. 18) extends through the slots 421, 423 and is slidably carried by the slots. The embodiment illustrated in FIGS. 14, 15 and 18 thus automatically changes the effective length of the support member to permit variations in the distance between the attachment locations of the support member above and below the ankle. For example, if the ankle is moved in the forward direction, the support member 415 pivots about the pivotal connector 420, the attachment pin 424 slides within the support member slot 421 and the slot member slot 423. Thus, the support member 415 is maintained in a proper position with respect to the ankle during normal movements thereof notwithstanding variations in the spacings between the pivotal connector 420 and the attachment pin 424 that may be caused by the ankle movement.

During flexing of the shoe 10, the support member 415 pivots about the pivotal connector 420 and the attachment pin 424 slides relative to the slots 421, 423.

Figure 17:
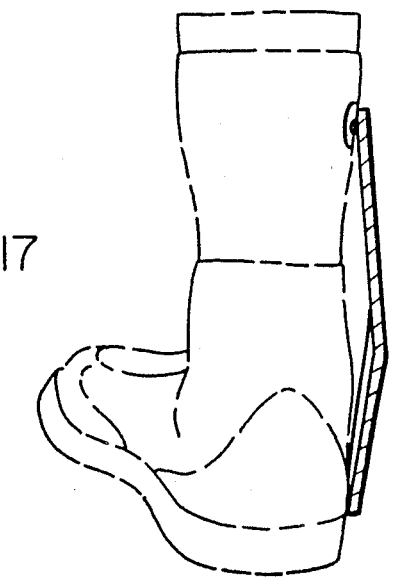
FIG. 17 is a rear elevational view of the shoe and the ankle support illustrated in FIG. 16.
Figure 16:
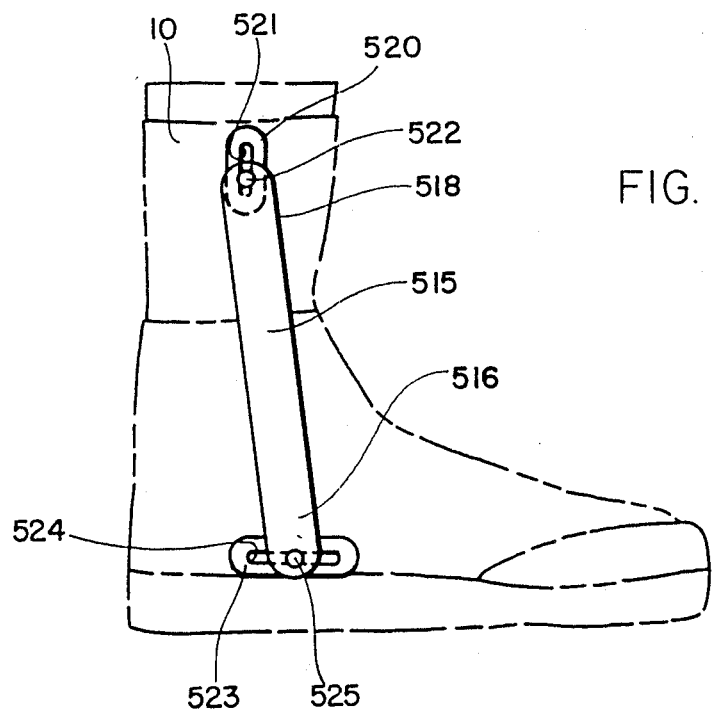
FIG. 16 is a side elevational view showing a shoe with yet another embodiment of the ankle support of the present invention mounted to the shoe.

In FIGS. 16 and 17, a further embodiment of the invention is illustrated and includes a rigid support member 515 secured to the shoe 10 for supporting the ankle 14 within the shoe 10 and having an upper end portion 518 and a lower end portion 516. A slot member 520 fixedly attached by adhesive or other appropriate securing means to the shoe 10 and has a slot 521 formed therein. An attachment pin 522 is fixedly connected to the upper end portion 518 and is slidably carried in the slot 521. A second slot member 523 fixedly attached by adhesive or other appropriate securing means to the shoe 10 has a slot 524 formed therein. A second attachment p;in 525 is fixedly attached by adhesive or other appropriate securing means to the lower end portion 516 and is slidably carried in the slot 524. The support member 515 includes a concave portion 526 to accommodate the outermost projection of the ankle 14. Specifically, the concave portion 526 opens toward the shoe 10 and its base is positioned along the support member 515 at a position relative to the outward bulge of the shoe 10 caused by the outermost projection of the ankle 14. Additionally, the support member 515 has a twisted shape and a centrally disposed curve for accommodating angular differences in the side of the leg and the side of the foot of the user.

Accordingly, the present invention provides an ankle support which permits a sufficiently wide range of movement of the ankle to render it suitable for protecting ankles against injury in even the most active sports, such as basketball, skiing, football or the like, and without unduly restricting the movement of the user participating in such sports. The embodiments of the ankle support of the present invention which automatically change the effective length between the attachment locations permit variations in the distance between the attachment locations above and below the ankle which increases the adaptability of the ankle support for ankle movement situations in which the spacing between the two attachment locations may vary by a relatively significant amount while continuing to maintain the support member at a proper position with respect to the ankle to prevent lateral bending thereof.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. An ankle support for preventing damage to a person's ankle through lateral bending of the ankle, said ankle support comprising a generally rigid elongate support member having an upper end and a lower end, retaining means for attaching said upper support end at a first attachment location above said ankle and for attaching said lower support end at a second attachment location below said ankle, and coupling means associated with at least one of said support members and said retaining means for automatically changing the effective length of said support member between said first and second attachment locations during normal movements of said ankle to permit variations in the distance between said first attachment location and said second attachment location, whereby said support member extends between said first and second attachment locations in an essentially straight line along a predetermined portion of said ankle to prevent lateral bending thereof and said support member is maintained at a proper position with respect to said ankle during normal movements thereof notwithstanding variation in the spacing of said first and second attachment locations that may be caused by said ankle movement.

2. An ankle support as defined in claim 1 and characterized further in that said support member includes an upper end piece and a separate lower end piece, and in that said coupling means includes a slot formed in one of said end pieces for slidably receiving and retaining the other of said end pieces, whereby said end pieces can move relative to one another to change said effective length of said support member.

3. An ankle support as defined in claim 1 and characterized further in that said retaining means includes attachment pin means associated with at least one of said ends of said support member and said coupling means includes slot means for slidably receiving and retaining said attachment pin means.

4. An ankle support as defined in claim 1 and characterized further in that said support member includes an upper end piece and a separate lower end piece, said coupling means includes a slot formed in one of said end pieces for slidably receiving and retaining the other of said end pieces, whereby said end pieces can move relative to one another to change said effective length of said support member, and said retaining means includes attachment pin means associated with at least one of said ends of said support member and said coupling means includes slot means for slidably receiving and retaining said attachment pin means.

5. An ankle support as defined in claim 1 and characterized further in that said support member includes a slot means and said retaining means includes a slot means and an attachment pin means slidably received and retained in both of said slot means.

6. An ankle support as defined in claim 1 and characterized further in that said coupling means includes a pair of slot means, one of said slot means being associated with a selected one of said upper support end and said first attachment location and the other of said slot means being associated with a selected one of said lower support end and said second attachment location, and in that said retaining means includes a pair of attachment pin means, one of said attachment pin means being slidably carried by said one slot means and associated with the other of said upper support end and said first attachment location, whereby said upper support end is movably coupled to said first attachment location, and the other of said attachment pin means being slidably carried by said other slot means and associated with the other of said lower support end and said second attachment location, whereby said lower support end is movably coupled to said second attachment location.

7. An ankle support prevention damage to a person's ankle through lateral bending of the ankle, said ankle support comprising a general rigid elongate support member having a generally elongate male sliding portion, and a generally elongate female sliding portion, and means for pivotally attaching said generally elongate male sliding portion at a respective one of a pair of attachment locations above and below said ankle, and means for pivotally attaching said generally elongate female sliding portion at the other of said pair of attachment locations above and below said ankle, said male sliding portion being slidably retained in said female sliding portion for sliding movement therein to automatically change the effective length of said support member between said attachment locations during normal movements of said ankle to permit variations in the distance between said attachment locations, whereby said support member extends between said attachment locations in an essentially straight line along a predetermined portion of said ankle to prevent lateral bending thereof and said support member is maintained at a proper position with respect to said ankle during normal movements thereof notwithstanding variation in the spacing of said first and second attachment locations that may be caused by said ankle movement.

8. An ankle support as defined in claim 7 and characterized further in that said means for pivotally attaching said generally elongate male sliding portion pivotally attaches said male sliding portion to said location below said ankle and said means for pivotally attaching said female sliding portion pivotally attaches said female sliding portion to said location above said ankle.

9. An ankle support as defined in claim 7 and characterized further in that one of said pivotal attaching means includes a slot and an attachment pin slidably carried in said slot, said attachment pin being connected to the respective male and female sliding portion associated with said one pivotal attaching means.

10. An ankle support as defined in claim 9 and characterized further in that said one pivotal attaching means is said male sliding portion pivotal attaching means.

11. An ankle support for preventing damage to a person's ankle through lateral bending of the ankle, said ankle support comprising a generally rigid elongate support member having an upper end and a lower end, said support member having a slot formed therein proximate a respective one of said ends and remote from the other of said ends, means for pivotally attaching said other end of said support member to a respective one of a pair of attachment locations above and below said ankle, means for attaching said one end of said support member at the other of said pair of attachment locations including a slot member fixedly attached at said other location, said slot member having a slot therein, and an attachment pin slidably carried in both said support member slot and said slot member slot whereby said support member extends between said attachment locations in an essentially straight line along a predetermined portion of said ankle to prevent lateral bending thereof and said support member is maintained at a proper position with respect to said ankle during normal movements thereof notwithstanding variation in the spacing of said first and second attachment location that may be caused by said ankle movement.

12. An ankle support as defined in claim 11 and characterized further in that said support member slot is formed proximate said lower end of said support member.

13. An ankle support for preventing damage to a person's ankle through lateral bending of the ankle, said ankle support comprising a generally rigid elongate support member having an upper end and a lower end, retaining means for attaching said upper support end at a first attachment location above said ankle and for attaching said lower support end at a second attachment location below said ankle, said retaining means including a pair of slot assemblies, each slot assembly for attaching a respective one of said ends of said support member to its associated attachment location and including a slot member having a slot, said slot member being located at a selected one of said respective one end of said support member and said associated attachment location, and an attachment pin slidably carried in said slot and connected to the other of said respective one end and said associated attachment location, whereby said support member extends between said attachment locations in an essentially straight line along a predetermined portion of said ankle to prevent lateral bending thereof and said support member is maintained at a proper position with respect to said ankle during normal movements thereof notwithstanding variation in the spacing of said first and second attachment locations that may be caused by said ankle movement.

14. An ankle support as defined in claim 13 and characterized further in that said slot members are located at the associated attachment locations of said ends of said support member.

15. An ankle support as defined in claim 13 and characterized further in that said support member includes a concave portion adapted to accommodate the extent of said ankle projecting thereinto.

16. An ankle support as defined in claim 13 and characterized further in that said ends of said support member are twisted relative to one another.

* * * * *

UNITED STATES PATENT AND TRADEMARK OFFICE
CERTIFICATE OF CORRECTION

PATENT NO. : 4,936,295

DATED : June 26, 1990

INVENTOR(S) : Larry A. Crane

It is certified that error appears in the above-identified patent and that said Letters Patent is hereby corrected as shown below:

Column 1, Line 9, after "4,809,686" add -- . --.

Column 1, Line 11, delete "The" and insert therefor -- In --.

Column 1, Line 33, delete "show" and insert therefor -- shoe --.

Column 2, Line 55, delete "to" and insert therefor -- of --.

Column 3, Line 5, delete "on" and insert therefor -- to --.

Column 4, Line 17, after "member 15" delete -- and --.

Column 4, Line 20, delete "in" and insert therefor -- if --.

Column 5, Line 5, delete "with" and insert therefor -- within --.

Column 5, Line 6, delete "than" and insert therefor -- then --.

Column 5, Line 63, delete "places" and insert therefor -- placed --.

Column 8, Line 64, delete "p;in" and insert therefor -- pin --.

Column 10, Line 52, delete "prevention" and insert therefor -- preventing --.

UNITED STATES PATENT AND TRADEMARK OFFICE
CERTIFICATE OF CORRECTION

PATENT NO. : 4,936,295

DATED : June 26, 1990

INVENTOR(S) : Larry A. Crane

It is certified that error appears in the above-identified patent and that said Letters Patent is hereby corrected as shown below:

Column 10, Line 54, delete "general" and insert therefor -- generally --.

Column 12, Line 2, delete "location" and insert therefor -- locations --.

Signed and Sealed this

Twenty-third Day of June, 1992

Attest:

DOUGLAS B. COMER

*Attesting Officer*  *Acting Commissioner of Patents and Trademarks*